United States Patent
Aoyagi et al.

(10) Patent No.: US 6,569,637 B1
(45) Date of Patent: May 27, 2003

(54) DIAGNOSTIC REAGENTS FOR RENAL FUNCTION DISORDERS AND METHOD FOR ANALYZING URINE SAMPLES

(75) Inventors: Kazumasa Aoyagi, Ibaraki (JP); Motoo Nakajima, Chiba (JP); Kenkiti Koiso, Ibaraki (JP)

(73) Assignee: Kikkoman Corporation, Noda (JP)

( * ) Notice: Subject to any disclaimer, the term of this patent is extended or adjusted under 35 U.S.C. 154(b) by 0 days.

(21) Appl. No.: 09/403,093

(22) PCT Filed: Apr. 17, 1998

(86) PCT No.: PCT/JP98/01768
§ 371 (c)(1),
(2), (4) Date: Oct. 15, 1999

(87) PCT Pub. No.: WO98/48044
PCT Pub. Date: Oct. 29, 1998

(30) Foreign Application Priority Data

Apr. 18, 1997 (JP) ............................................. 9-116091

(51) Int. Cl.⁷ ................................................. C12Q 1/66
(52) U.S. Cl. ............................................. 435/8; 435/21
(58) Field of Search ....................................... 435/8, 21

(56) References Cited

U.S. PATENT DOCUMENTS 3,616,253 A * 10/1971 D'Eustachio
3,971,703 A * 7/1976 Picciolo et al.
4,014,745 A * 3/1977 Fletcher et al.
5,759,795 A * 6/1998 Jubin

FOREIGN PATENT DOCUMENTS

WO  96/02666  2/1996

OTHER PUBLICATIONS

Bernstein et al.; "Urinary Adenylate Kinase and Urinary Tract Infections"; Journal of Clinical Microbiology; vol. 18, No. 3; Sep. 1983; pp. 578–584.

* cited by examiner

Primary Examiner—Ralph Gitomer
(74) Attorney, Agent, or Firm—Foley & Lardner

(57) ABSTRACT

The present invention aims at providing a reagent and a method for simply, rapidly, and accurately diagnosing renal dysfunction.

According to the present invention, free ATP in a urine sample from a patient suffering from renal dysfunction is determined by a bioluminescent technique using luciferin and luciferase. By determining the value, it is possible to simply, rapidly, and accurately diagnose common renal dysfunction. Moreover, according to the present invention, it is possible to avoid renal dysfunction caused by side-effects of drugs, by collecting daily the urine of a patient who has been administered with carcinostatic that is toxic to kidney such as cisplatin or methotrexate, and analyzing the changes in the ATP level in the urine sample by a bioluminescent technique, thereby detecting hypersensitivity of the patient caused by such drug or by an excessive administration of such drug, or thereby determining an optimal dose (a maximum acceptable dose) of such drug.

4 Claims, 3 Drawing Sheets

Change in NAG activity in a urine sample
before and after cisplatin administration Change in $\beta_2$MG level in a urine sample
before and after cisplatin administration

DIAGNOSTIC REAGENTS FOR RENAL FUNCTION DISORDERS AND METHOD FOR ANALYZING URINE SAMPLES

TECHNICAL FIELD

The present invention relates to a reagent for diagnosing renal dysfunction, which contains luciferin and luciferase. The present invention also relates to a method for analyzing a urine sample, which is useful to diagnose renal dysfunction and to determine an optimal dose of a nephrotoxic drug, the method including determining free adenosine 5'-triphosphate (hereinafter, referred to as "ATP") in the urine sample by a bioluminescence technique using the above-mentioned diagnostic reagent.

BACKGROUND ART

As a conventional method for diagnosing renal dysfunction, for example, the following methods are known: a method in which urea in a blood sample is determined (JP-B-61-47382); a method in which creatinine in a blood sample is determined (JP-B-60-38666); and a method in which albumin and an albumin degradation substance in a urine sample are determined (JP-A-5-302922).

Although numbers of methods are known for diagnosing renal dysfunction by determining components in a urine or a blood sample, such methods are disadvantageous in that they take time to obtain the results of the determination.

In the field of clinical medicine, many drugs are known to be toxic to kidney. In particular, cisplatin, which is frequently used in chemotherapy (a major therapy for patients with urinary carcinoma) has an excellent carcinostatic action but yet it has strong toxicity to kidney. Therefore, excessive administration of cisplatin arises a risk of causing serious effects on the treatment of a patient.

Accordingly, it is known to avoid the side-effects as much as possible by detecting hypersensitivity of a patient caused by such drug or by an excessive administration of such drug, determining an optimal dose (a maximum acceptable dose) of such drug, and analyzing increase and decrease of metabolite $\beta_2$-microglobulin (hereinafter, referred to as "$\beta_2$-MG") that usually appears in urine or $\beta$-N-acetyl-D-glucosaminidase (hereinafter, referred to as "NAG") contained in a urine sample.

However, the above-mentioned methods are disadvantageous in that they take time to obtain the results of the determination and in that they have some other drawbacks. Thus, they have not yet met the needs.

Specifically, the method of measuring the metabolite $\beta_2$-MG in a urine sample requires an expensive reagent and a special device. The method of measuring an NAG activity in a urine sample by using p-nitrophenyl-$\beta$-D-glucosaminide as a substrate or by using cresolsulfonphthaleinyl-N-acetyl-$\beta$-D-glucosaminide as a substrate employs a calorimetric analysis that has drawbacks such as low sensitivity and a wide reference value that does not allow diagnosis unless the progress of the renal dysfunction is severe enough.

DISCLOSURE OF THE INVENTION

Thus, the present invention aims at providing a method that can be used for diagnosing renal dysfunction and for determining an optimal dose of a drug that is toxic to kidney, and aims at providing a reagent used in the method.

In order to solve the above problem, the present inventors have undergone intensive studies and directed their attention on free ATP contained in a urine sample of a patient suffering from renal dysfunction. They determined the free ATP based on bioluminescence using luciferin/luciferase luminescent reagent, and noticed that the ATP levels in the urine of the patient suffering from common renal dysfunction is likely to be high, finding significant difference between the ATP level of the patient and that of a healthy individual. Accordingly, they found out that ATP can be used as an index for diagnosing renal dysfunction, and that renal dysfuction can be diagnosed by accurately determining free ATP in a urine sample in a short time by a very simple operation. Furthermore, they collected daily the urine from patients who have been administered with carcinostatic such as cisplatin or methotrexate that is toxic to kidney. The urine samples were added with ATP to react therewith for a prescribed period of time and the ATP levels in the urine samples were measured using luciferin and luciferase. The obtained ATP levels and a control ATP level obtained before the reaction were compared to determine the ATP degradation activities in the urine samples. These activities were found to correlate well with that of the conventional diagnoses for renal dysfunction based on changes in NAG activities or $\beta_2$-MG in urine samples. Similarly, urine samples were added with adenosine 5'-diphosphate (hereinafter, referred to as "ADP") to react therewith for a prescribed period of time, and the ATP levels in the urine samples were measured using luciferin and luciferase. The obtained ATP levels and a control ATP level obtained before the reaction were compared to determine the ATP production activities of the urine samples. These activities were also found to correlate well with that of the conventional diagnoses for renal dysfunction.

The present invention was completed based on the above-described findings.

The first aspect of the present invention provides a diagnostic reagent for renal dysfunction, comprising luciferin and luciferase.

The second aspect of the present invention provides a method for analyzing a urine sample, comprising the steps of reacting luciferin and luciferase with a urine sample and determining the amount of free ATP in the urine sample; a method for analyzing a urine sample, comprising the steps of adding ATP to a urine sample for reaction for a certain period of time, determining the amount of ATP in the urine sample using luciferin and luciferase, and comparing the determined ATP amount to an ATP amount of a control obtained before the reaction; and a method for analyzing a urine sample, comprising the steps of adding ADP to a urine sample for reaction for a certain period of time, determining the amount of ATP in the urine sample using luciferin and luciferase, and comparing the determined ATP amount to an ATP amount of a control obtained before the reaction.

The third aspect of the present invention provides a diagnostic kit for renal dysfunction, comprising (i) a diagnostic reagent for renal dysfunction containing luciferin and luciferase, (ii) a buffer solution for diluting a urine sample, and (iii) ATP standard reagent; and a diagnostic kit for renal dysfunction, comprising (i) a diagnostic reagent for renal dysfunction containing luciferin and luciferase, (ii) a buffer solution for diluting a urine sample, and (iii) ADP standard reagent.

The fourth aspect of the present invention provides a diagnostic method for renal dysfunction, comprising the steps of reacting luciferin and luciferase with a urine sample and determining the amount of free ATP in the urine sample; a diagnostic method for renal dysfunction comprising the steps of adding ATP to a urine sample for reaction for a certain period of time, determining the amount of ATP in the urine sample using luciferin and luciferase, and comparing the determined ATP amount to an ATP amount of a control obtained before the reaction; and a diagnostic method for renal dysfunction comprising the steps of adding ADP to a urine sample for reaction for a certain period of time, determining the amount of ATP in the urine sample using luciferin and luciferase, and comparing the determined ATP amount to an ATP amount of a control obtained before the reaction.

The fifth aspect of the present invention provides a use of a composition for diagnosing renal dysfunction, comprising luciferin and luciferase.

Hereinafter, the present invention will be described in more detail.

A diagnostic reagent for renal dysfunction according to the invention is prepared by dissolving luciferin, luciferase and magnesium ion (or other metal ions) in a suitable buffer. Preferably, the diagnostic reagent of the invention is a commercially available product such as "CheckLite™", an ATP measurement kit available from Kikkoman Corp.

Preferable concentration ranges of components in the diagnostic reagent of the invention are shown below. Although the diagnostic reagent may be used directly, it is preferable to freeze-dry the reagent before use so that its storage stability is remarkably enhanced and it can be stored for a year or longer.

Luciferin: 1.0 $\mu$M (final concentration) or higher, particularly, 10–10,000 $\mu$M (final concentration).
Luciferase: 0.01 mg (final concentration) or higher, particularly, 0.1–20 mg/ml (final concentration).
Magnesium ion: 0.1 mM (final concentration) or higher, particularly, 1.0–50 mM/ml (final concentration).
Buffer (e.g., Tricine buffer solution): 1 mM (final concentration) or higher, particulaly, 10–100 mM (final concentration).

The luciferase used herein may be: luciferase derived from, for example *Luciola cruciata, Luciola Lateralis, Photinus pyralis* or the like; such luciferase produced by genetic recombination; or luciferase produced by genetic recombination using luciferase gene which has partial mutation, substitution or modification therein.

Besides Tricine buffer solution, the buffer may be, for example, HEPES buffer solution, Tris-HCl buffer solution, phosphate buffer solution, Bis-Tris-Propane buffer solution or MES buffer solution.

Preferable concentrations are identical to those of Tricine buffer solution mentioned above. Preferably, pH is in a range of 6.5 to 8.5.

The diagnostic reagent of the invention may be added with various compounds in order to facilitate an enzyme reaction and a luminescent reaction.

Examples of such compounds include bovine serum albumin, dithiothreitol and stabilizers such as EDTA.

In one aspect of a method for analyzing a urine sample according to the invention, a urine sample is reacted with the above-described diagnostic reagent, and then free ATP level in the urine sample is determined by a bioluminescent technique.

According to the present invention, the urine sample is used directly, or after being suitably diluted with water, buffer solution or the like.

Although pH is not necessarily adjusted, it is preferable to adjust the pH to 4–10 with a suitable pH adjuster such as hydrochloric acid, sulfuric acid, nitric acid, sodium hydroxide and potassium hydroxide.

Preferably, "Lumitester K-210", a luminometer available from Kikkoman Corp. is used for determining the luminescent level.

According to this method, free ATP in a urine sample can be determined accurately and rapidly, enabling diagnosis for renal dysfunction.

Specifically, according to the clinical tests conducted by the present inventors, an average concentration of free ATP in urine samples from 48 patients suffering from common renal dysfunction was $3.6 \times 10^{-8}$ M which was significantly different from that obtained from 39 healthy individuals ($1.4 \times 10^{-8}$ M). This indicates that free ATP in urine samples can be an effective marker in a diagnosis of renal dysfunction.

In another aspect of a method for analyzing a urine sample according to the invention, a urine sample is added with ATP and reacted therewith for a prescribed period of time, and then the ATP level in the urine sample is measured by a bioluminescent technique using the above-described diagnostic reagent. Then, the ATP level is compared to that of a control sample obtained before the reaction.

The concentration of the ATP to be added is $10^{-9}$ M to $10^{-3}$ M, more preferably $1 \times 10^{-8}$ M to $5 \times 10^{-5}$ M, and most preferably $5 \times 10^{-8}$ M to $5 \times 10^{-6}$ M.

The urine sample is left for a predetermined period of time after being added with ATP so that ATP is decomposed with ATP degradation enzymes contained in the urine sample.

ATP degradation enzymes are contained in cells of organisms and usually are not excreted in urine. Therefore, when a urine sample from a healthy individual is added with ATP and left for a prescribed time, a reduction in the ATP concentration thereof is little. On the other hand, when a kidney sustains dysfunction due to administration of a drug toxic to kidney or due to other diseases, the ATP degradation activity in a urine sample thereof increases, in which case the concentration of the ATP is reduced.

Thus, renal dysfunction, particularly an effect of a drug toxic to a kidney, can be diagnosed by measuring the reduction level of the ATP concentration after a prescribed period of time.

The reaction temperature is preferably 15–50° C., more preferably 25–45° C., and most preferably 30–40° C.

The reaction time is preferably 30 seconds to 120 minutes, more preferably 2–60 minutes, and most preferably 5–40 minutes.

After the prescribed period of time of reaction, the ATP concentration in the urine sample changes (is reduced) due to the action of the ATP degradation enzymes in the urine sample. The ATP concentration is determined by the above-described bioluminescent technique.

Similarly, an ATP concentration of a control urine sample before the reaction is also determined by the bioluminescent technique.

Renal dysfunction is diagnosed by comparing the ATP concentrations before and after the reaction.

The comparison is conducted by determining the ratio of the ATP concentration after the reaction to that before the reaction (residual ATP % (percentage)). According to this diagnosis, low residual ATP percentage represents a patient suffering from renal dysfunction while high residual ATP percentage represents a healthy individual.

According to the clinical tests conducted by the present inventors, an average residual ATP percentage obtained after the ATP degradation was about 83% in urine samples from 48 patients suffering from renal dysfunction which was clearly distinct from that in urine samples from healthy individuals (93%).

In yet still another aspect of a method for analyzing a urine sample according to the invention, a urine sample is added with ADP and reacted therewith for a prescribed period of time, and then the ATP level in the urine sample is determined by a bioluminescent technique using the above-described diagnostic reagent. Then, the obtained ATP level is compared to that of a control sample before the reaction.

The concentration of the ADP to be added is $10^{-9}$ M to $10^{-3}$ M, more preferably $1 \times 10^{-8}$ M to $5 \times 10^{-5}$ M, and most preferably $5 \times 10^{-8}$ M to $5 \times 10^{-6}$ M.

The urine sample is left for a predetermined period of time after being added with ADP so that ATP is produced from ADP by adenylate kinase contained in the urine sample.

Adenylate kinase-like activity is considered to be generated by disruption of the renal tubule cells. Accordingly, when a urine sample from a healthy individual is added with ADP and left for a prescribed period of time, an increase in the ATP concentration thereof is little. On the other hand, when a kidney sustains dysfunction due to administration of a drug toxic to kidney or due to other diseases, the adenylate kinase-like activity thereof increases, in which case the concentration of the ATP is increased.

Accordingly, renal dysfunction, particularly an effect of a drug toxic to kidney, can be diagnosed by determining the increase of the ATP concentration after a prescribed period of time.

The reaction temperature is preferably 15–50° C., more preferably 25–45° C., and most preferably 30–40° C.

The reaction time is preferably 30 seconds to 120 minutes, more preferably 2–60 minutes, and most preferably 5–40 minutes.

After the prescribed period of time of reaction, the ATP concentration in the urine sample changes (is increased) due to the adenylate kinase-like activity in the urine sample. The ATP concentration is determined by the above-described bioluminescent technique.

Similarly, an ATP concentration of a control urine sample before the reaction is also determined by the bioluminescent technique.

Renal dysfunction is diagnosed by comparing the ATP concentrations before and after the reaction.

The comparison is conducted by determining the ratio of the ATP concentration after the reaction to that before the reaction (ATP production %).According to this diagnosis, high ATP production represents a patient suffering from renal dysfunction while low ATP production represents a healthy individual.

BEST MODE FOR PRACTICING THE INVENTION

Figure 1:
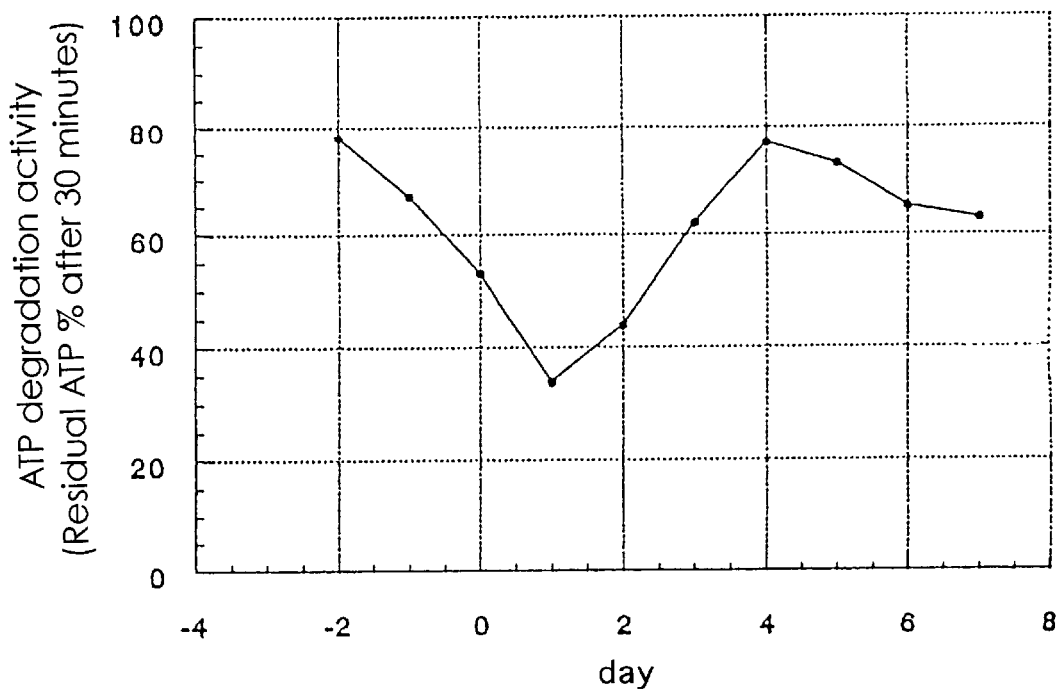
FIG. 1 is a diagram showing the change in ATP degradation activity in a urine sample before and after cisplatin administration.

The present invention will be explained in detail below by means of examples.

EXAMPLE 1

Preparation of Diagnostic Reagent for Renal Dysfunction

Preparation Example 1

A diagnostic reagent for renal dysfunction was prepared by dissolving and mixing the following components in 25 mM Tricine buffer(pH7.75) at the respective final concentrations.

Components

Luciferin: 100 μM

Luciferase: 0.1 mg

Magnesium sulfate: 5 mM

Preparation Example 2

A diagnostic reagent for renal dysfunction was prepared by dissolving and mixing the following components in 25 mM Tricine buffer(pH7.75) at the respective final concentrations.

Components

Luciferin: 150 μM

Luciferase: 0.1 mg

Magnesium sulfate: 6 mM

EXAMPLE 2

Analysis of Urine Sample (1)

A urine sample obtained from a patient suffering from common renal dysfunction was 10-fold diluted with 20 mM phosphate buffer (pH7.75). Two hundreds μl of the diluted solution was transferred into a test tube for ATP measurement. Then, 100 μl of the diagnostic reagent prepared in Example 1 (Preparation Example 1) was added to the solution in the tube, and the luminescence was immediately determined using Lumitester K-210. The concentration of free ATP in the urine sample was determined referring to a standard calibration curve which had been prepared in advance from ATP reagent of known concentrations and the luminescent levels thereof.

The average concentration of free ATP in the urine samples obtained from 48 patients with renal dysfunction was $3.6 \times 10^{-8}$M which was significantly different from that of 39 healthy individuals ($4 \times 10^{-8}$M). This result showed that free ATP in a urine sample could be an effective marker for use in diagnosis of renal dysfunction.

EXAMPLE 3

Analysis of a Urine Sample (2)

An ATP standard reagent was prepared by dissolving sodium salt of ATP in 25 mM HEPES buffer (pH7.75) at a concentration of $2 \times 10^{-6}$M.

Two-hundreds μl of a urine sample obtained from a patient suffering from renal dysfunction who received cisplatin administration was added and reacted with 200 μl of the ATP standard reagent prepared as described above at 37° C. for 30 minutes.

The solution was 10-fold diluted with 20 mM phosphate buffer (pH7.5), and 200 μl of the diluted solution was transferred into a test tube for ATP measurement. Then, 100 μl of luciferin-luciferase luminescent reagent which had been prepared by dissolving the freeze-dried luminescent reagent (included in ATP assay kit "CheckLite™" available from Kikkoman Corporation) in a solution for dissolving the reagent (also included in the kit) was added to the solution in the tube. The luminescent level based on the ATP level remaining after the reaction was immediately determined using Lumitester K-210.

On the other hand, the luminescent level corresponding to the ATP level in a urine sample before the reaction was determined in the same matter.

Diagnosis of renal dysfunction by ATP method was performed by calculating the ATP index (residual ATP %)

according to the equation below and determining whether the subject is a patient with renal dysfunction S or a healthy individual R according to the following criteria.
(Criteria for Distinguishing between Presence (S) and Absence (R) of Renal Dysfunction)

$$ATP\text{index} = (Y/X) \times 100\%$$

X=luminescent level before the reaction
Y=luminescent level after the reaction
ATP index<75%: patient with renal dysfunction (S)
ATP index≦75%: healthy individual (R)
Those results are shown in FIG. 1.

Comparative Example 1

NAG activity in a urine sample was determined by cresolsulfonphthaleinyl-N-acetyl-β-D-glucosaminide substrate method. See *The Japanese journal of clinical medicine*, vol. 47, extra issue, pp.363–365 (1989) and *The Japanese Journal of clinical pathology*, special number vol.56, pp. 90–101 (1983).

Figure 2:
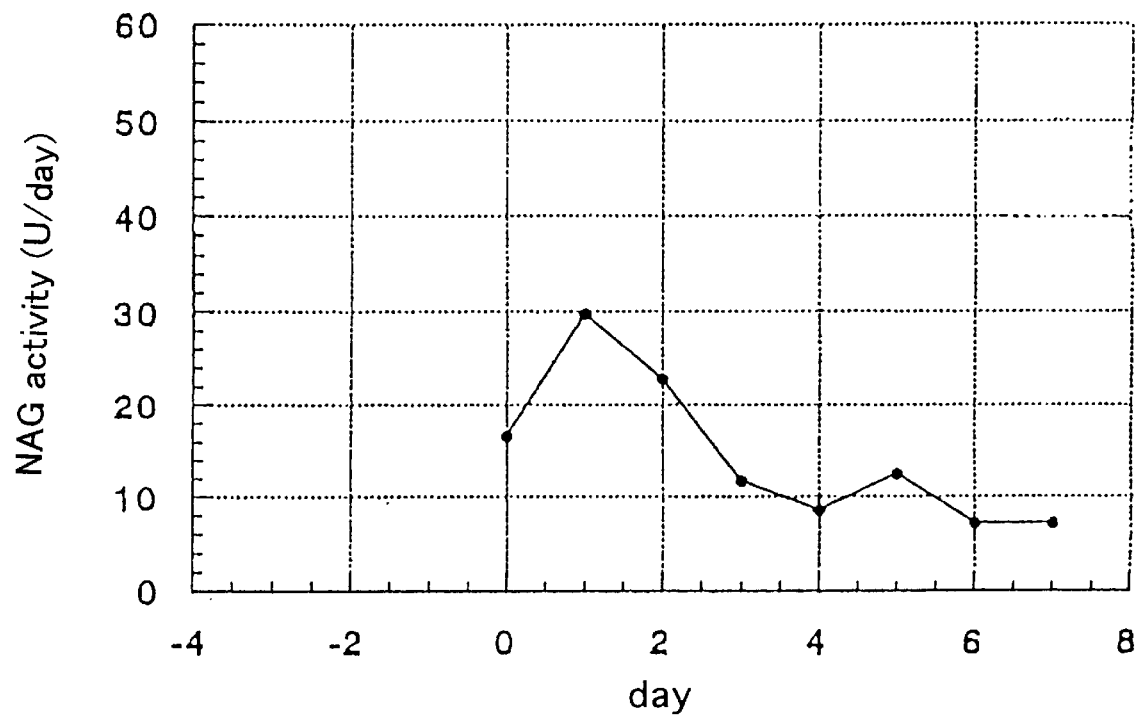
FIG. 2 is a diagram showing the change in NAG activity in a urine sample before and after cisplatin administration.

The result is shown in FIG. 2.

Comparative Example 2

β2-MG level in a urine sample was determined by radioimmunoassay double-antibody assay (RIA double-antibody assay). See *The Japanese journal of nuclear medicine*, vol. 14, pp.877–885 (1977).

Figure 3:
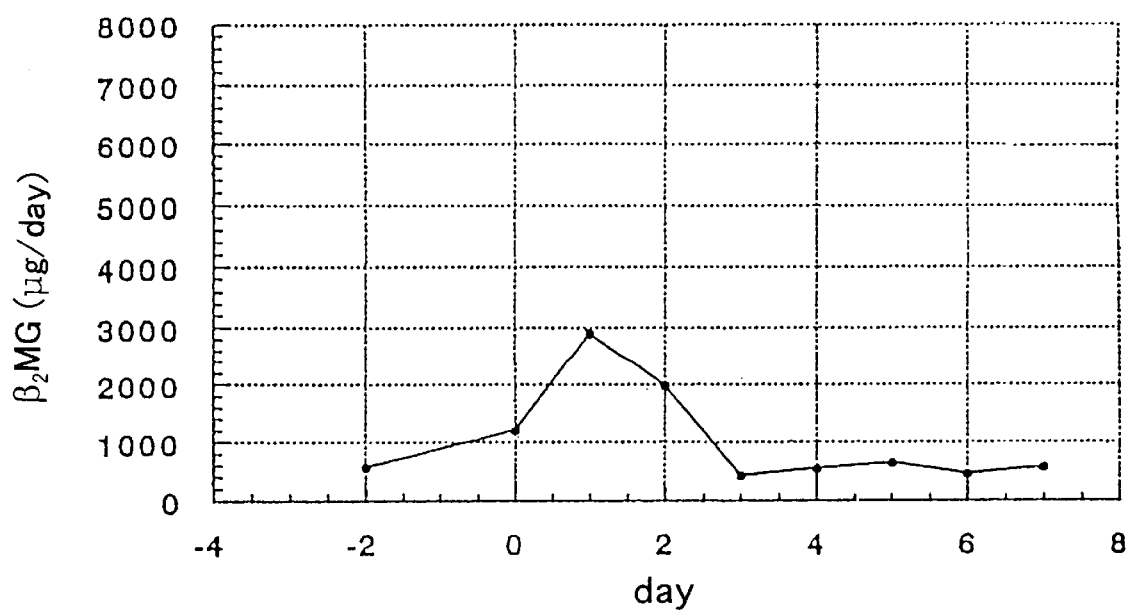
FIG. 3 is a diagram showing the change in $\beta_2$MG level in a urine sample before and after cisplatin administration.

The result is shown in FIG. 3.

The result shown in FIG. 1 indicates that when cisplatin is administered to a patient with renal dysfunction, residual ATP % in his/her urine sample decreases to the minimum (i.e., ATP degradation activity in the urine sample is maximum) one day after the administration. By daily examination of the ATP degradation activities before and after the administration, the ATP degradation activity pattern (FIG. 1) was consistent with those of NAG activity and β$_2$-MG level determined by the standard methods (FIGS. 2 and 3). Particularly, the change in the activity pattern was prominent.

Accordingly, examining a change in ATP degradation activity facilitates the discovery of an excessive administration of said cartinostatic and a detection of a nephrotoxicity of the drug against the patient, and thus allows to determine the optimum dose (maximum permissive dose) of those drugs for the individual so as to avoid renal disorder due to side-effects of the drugs.

EXAMPLE 4

Analysis of a Urine Sample (3)

An ADP standard reagent was prepared by dissolving potassium salt of ADP in 25 mM HEPES buffer (pH7.75) at a concentration of 1 mM.

A urine sample obtained from a patient suffering from renal dysfunction was 10-fold diluted with 25 mM HEPES buffer, and 100 μl of the diluted solution was added with 100 μl of the ADP standard reagent and then 100 μl of the diagnostic reagent prepared in Example 1(Preparation Example 1). Immediately after that, the luminescent level corresponding to the ATP generated was determined at 10 second intervals using Lumat LB-9501 (available from Berthold Corporation).

Adenylate kinase-like activity which produces ATP from ADP was detected in the urine sample from renal dysfunction patient.

The same assay was performed on a urine sample from a normal individual. Little increase in the luminescent level due to the ATP generation from ADP was recognized.

Those results showed that the adenylate kinase-like activity could have been generated due to the disruption of renal tubule cells. Thus, it was proved that the adenylate kinase-like activity could be an effective marker for indicating renal dysfunction.

INDUSTRIAL APPLICABILITY

According to the present invention, a reagent and a method are provided which enables accurate diagnosis for renal dysfunction in time as short as 30 seconds to 120 minutes by a very simple operation.

It is possible to avoid renal dysfunction caused by side-effects of drugs, by collecting daily the urine from a patient who has been administered with carcinostatic that is toxic to kidney such as cisplatin or methotrexate, and analyzing the changes in the ATP level in the urine sample by a bioluminescent technique, thereby detecting hypersensitivity of the patient caused by such drug or by an excessive administration of such drug, or thereby determining an optimal dose (a maximum acceptable dose) of such drug.

What is claimed is:

1. A diagnostic method for determining renal dysfunction by measuring ATPase activity in a urine sample, comprising adding ATP to said urine sample, allowing said ATP to react for 0.5 to 120 minutes, determining the amount of free ATP in the urine sample using luciferin and luciferase, and comparing the determined free ATP amount to a free ATP amount before the reaction.

2. The method of claim 1, wherein 10–10,000 μM of luciferin, 0.1–20 mg/ml of luciferase, and $1 \times 10^{-9}$ to $1 \times 10^{-3}$ M of ATP are added to the urine sample.

3. The method of claim 1, wherein $1 \times 10^{-8}$ to $5 \times 10^{-5}$ M of ATP is added to the urine sample.

4. The method of claim 1, wherein $5 \times 10^{-8}$ to $5 \times 10^{-6}$ M of ATP is added to the urine sample.

* * * * *